United States Patent [19]
Kadono et al.

[11] Patent Number: 6,017,875
[45] Date of Patent: Jan. 25, 2000

[54] HIGHER SECONDARY ALCOHOL ALKOXYLATE COMPOUND COMPOSITION, METHOD FOR PRODUCTION THEREOF, AND DETERGENT AND EMULSIFIER USING THE COMPOSITION

[75] Inventors: Yukio Kadono; Kunihiko Kimata; Kenji Rakutani, all of Kanagawa; Yoshiyuki Onda, Osaka, all of Japan

[73] Assignee: Nippon Shokubai Co., Ltd., Osaka, Japan

[21] Appl. No.: 08/985,463

[22] Filed: Dec. 5, 1997

[30] Foreign Application Priority Data

| Dec. 6, 1996 | [JP] | Japan | 8-327365 |
| Dec. 6, 1996 | [JP] | Japan | 8-327366 |
| Mar. 7, 1997 | [JP] | Japan | 9-053212 |
| Mar. 7, 1997 | [JP] | Japan | 9-053213 |

[51] Int. Cl.$^7$ ............... C11D 9/00; C11D 17/00; C11D 1/72
[52] U.S. Cl. ............... 510/506; 510/356; 510/413; 516/57
[58] Field of Search ............... 510/356, 506, 510/413

[56] References Cited

U.S. PATENT DOCUMENTS

| 3,376,333 | 4/1968 | Ernst et al. | 260/458 |
| 4,139,566 | 2/1979 | Kim et al. | 568/679 |
| 4,371,716 | 2/1983 | Paxson et al. | 568/678 |

FOREIGN PATENT DOCUMENTS

| 0 310 194 | 4/1989 | European Pat. Off. . |
| 0 310 194 | 5/1989 | European Pat. Off. . |
| 51-17538 | 6/1976 | Japan . |
| 59-175463 | 10/1984 | Japan . |
| 111296 | 12/1964 | Netherlands . |
| 6401246 | 8/1965 | Netherlands . |
| 1103629 | 2/1968 | United Kingdom . |

OTHER PUBLICATIONS

Bakker et al., "Sulfonates and sulfates of sec–alkyl ethyl ether: detergents prepared by the addition of substituted alcohols to 1–alkenes", Chim.Phys.Appl.Prat.Ag.Surfact., Compte Rendue Cong. Int. Deterg. 5th, Sep. 9–13, 1968, pp. 157–165 XP002075332.

Knifton et al., "Detergent–range alcohol alkoxylates via vicinal glycol additions to alpha–olefins", Applied Catalysis, A, vol. 130, 1995, pp. 79–88 XP002075333.

Bakker et al., "An exploratory study of the addition reactions of ethyleneglycol, 2–chloroethanol and 1,3–dichloro–2–propanol to 1–dodecene", Journal of the American Oil Chemists' Society, vol. 44, Sep. 1967 pp. 517–521 XP002058548.

P.M. Bakker, "An Exploratory Study of the Addition Reactions of Ethyleneglycol, 2–Chloroethanol and 1,3–Dichloro–2–Propanol to 1–Dodecene", vol. 44, Sep. 1967, pp. 517–521.

*Primary Examiner*—Yogendra Gupta
*Assistant Examiner*—John M. Petruncio
*Attorney, Agent, or Firm*—Fish & Richardson P.C.

[57] ABSTRACT

A higher secondary alcohol alkoxylate compound composition represented by the general formula (1):

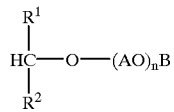

(1)

[wherein $R^1$ and $R^2$ represent an alkyl group provided that the total number of carbon atoms of $R^1$ and $R^2$ is in the range of 7 to 29 and the number of carbon atom of $R^2$ is not less than that of $R^1$ (the number of carbon atom of $R_1 \leq$ the number of carbon atom of $R_2$), A represents a lower alkylene group, n represents a numeral in the range of 1 to 50 on the average; providing that when n is not less than 2, the number of species of oxyalkylene group represented by AO may be either one or two or more, and that when the oxyalkyl groups have two or more species, all the oxyalkylene groups are present in the average of n, and B represents a hydrogen atom or $SO_3M$ (wherein M represents an alkali metal atom, an alkaline earth metal atom, an ammonium group or a substituted ammonium group)], wherein the composition comprises 30 to 90 mol % of the higher secondary alcohol alkoxylate compound (X) having a methyl group for $R^1$ and 70 to 10 mol % of the higher secondary alcohol alkoxylate compound (Y) having an alkyl group of 2 or more carbon atoms for $R^1$, a method for the production thereof, and a detergent and an emulsifier using the composition.

15 Claims, 10 Drawing Sheets

HIGHER SECONDARY ALCOHOL ALKOXYLATE COMPOUND COMPOSITION, METHOD FOR PRODUCTION THEREOF, AND DETERGENT AND EMULSIFIER USING THE COMPOSITION

BACKGROUND OF THE INVENTION

1. Field of the Invention

The present invention relates to a higher secondary alcohol alkoxylate compound composition, a method for the production thereof, and a detergent and an emulsifier using the composition.

2. Description of the Related Art

The nonionic surfactants include alkyl phenol ethoxylates, higher primary alcohol ethoxylates, fatty acid ethoxylates, and etc.

Among these nonionic surfactants, the alkyl phenol ethoxylates, particularly nonyl phenol ethoxylates, are fated to incur growing restrictions because they are deficient in biodegradability and consequently are apt to exert adverse effects on the environment.

The higher primary alcohol ethoxylates are at a disadvantage not only in solidifying at room temperature on account of high pour points but also in exhibiting a deterging power and an emulsifying power hardly deserving to be called satisfactory on account of deficiency in surface active properties such as the permeating power.

Some of the other nonionic surfactants such as, for example, fatty acid ethoxylates, incur restrictions of use such as the inability to be effectively used in an alkaline state because they succumb to hydrolysis and none of them are fully satisfactory in quality.

The higher secondary alcohol ethoxylates as the nonionic surfactant are at an advantage in manifesting low pour points, permitting easy handling, exhibiting a highly satisfactory permeating power, inducing perfect extinction of foam, excelling in deterging power and emulsifying power, and proving to be useful.

For the conventional method, however, they are produced by the steps of subjecting a straight chain paraffin formed of one member or a mixture of two or more members selected from the group consisting of hydrocarbons of 8 to 20 carbon atoms to liquid phase oxidation thereby forming a random secondary alcohol, adding ethylene oxide to the random secondary alcohol by the use of a Lewis acid catalyst thereby obtaining a low ethylene oxide adduct, recovering the unaltered alcohol from the resultant reaction mixture, and further adding ethylene oxide to the low ethylene oxide adduct by the use of a basic catalyst.

Thus, the production of the ethoxylate requires not only just one round of addition of ethylene oxide but also other steps such as removal of catalyst, distillation, and further addition of ethylene oxide.

This process, therefore, is highly complicated so long as this method of production is concerned.

The anionic surfactants include alkyl aryl sulfonates, higher primary alcohol sulfuric esters, higher primary alkyl ether sulfuric esters, etc.

In these anionic surfactants, the alkyl aryl sulfonates, particularly straight chain alkyl benzene sulfonates, are fated to incur growing restrictions because they are deficient in biodegradability and consequently exert adverse effects on the environment.

The alkyl aryl sulfonates, the higher primary alcohol sulfuric esters, etc. are easily affected by the hardness of water and deficient in water-solubility.

The higher primary alkyl ether sulfuric esters are at a disadvantage not only in manifesting high viscosity and easily subjected to gelation but also in being deficient in such surface active properties as surface tension and permeating power and exhibiting a deterging power and an emulsifying power hardly deserving to be called satisfactory.

None of the other anionic surfactants is fully satisfactory in terms of quality.

The higher secondary alkyl ether sulfuric esters as the anionic surfactants do not easily succumb to gelation owing to low viscosity and, therefore, permit easy handling, exhibit highly satisfactory surface tension and permeating power, induce perfect extinction of foam, excel in deterging power and emulsifying power, and prove to be useful.

By the conventional method, however, they are produced by the steps of subjecting a straight chain paraffin formed of one member or a mixture of two or more members selected from the group consisting of hydrocarbons of 8 to 20 carbon atoms to liquid phase oxidation thereby forming a random secondary alcohol, adding ethylene oxide to the random secondary alcohol by the use of a Lewis acid catalyst thereby obtaining a low ethylene oxide adduct, recovering the unaltered alcohol from the resultant reaction mixture, further adding ethylene oxide to the low ethylene oxide adduct by the use of a basic catalyst, and subsequently sulfating the resultant adduct by the use of chlorosulfonic acid and sulfuric anhydride.

Thus, the production of the higher secondary alkyl ether sulfuric ester requires not only just one round of addition of ethylene oxide but also other steps such as removal of catalyst, distillation, further addition of ethylene oxide, and sulfation.

This process, therefore, is highly complicated so long as this method of production is concerned.

An object of this invention, therefore, is to provide a novel higher secondary alcohol alkoxylate compound composition, a method for the production thereof, and a deterging agent and an emulsifying agent using the composition.

Another object of this invention is to provide a higher secondary alcohol alkoxylate compound composition having a low pour point, permitting easy handling, exhibiting a satisfactory permeating power, inducing perfect extinction of foam, and excelling in deterging power and emulsifying power, a method for the production thereof, and a detergent and an emulsifier using the composition.

SUMMARY OF THE INVENTION

The objects mentioned above are accomplished by a higher secondary alcohol alkoxylate compound composition represented by the general formula (1):

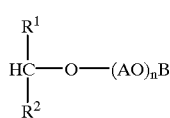

(1)

[wherein $R^1$ and $R^2$ represent an alkyl group provided that the total number of carbon atoms of $R^1$ and $R^2$ is in the range of 7 to 29 and the number of carbon atom of $R^2$ is not less than that of $R^1$ (the number of carbon atom of $R_1 \leq$ the number of carbon atom of $R_2$), A represents a lower alkylene group, n represents a numeral in the range of 1 to 50 on the average; providing that when n is not less than 2, the number of species of oxyalkylene group represented by AO maybe either one or two or more, and that when the oxyalkyl groups have two or more species, all the oxyalkylene groups are present in the average of n, and B represents a hydrogen atom or $SO_3M$ (wherein M represents an alkali metal atom, an alkaline earth metal atom, an ammonium group or a substituted ammonium group)], wherein the composition comprises 30 to 90 mol % of the higher secondary alcohol alkoxylate compound (X) having a methyl group for $R^1$ and 70 to 10 mol % of the higher secondary alcohol alkoxylate compound (Y) having an alkyl group of 2 or more carbon atoms for $R^1$.

The objects mentioned above are accomplished by a detergent formed by incorporating therein a higher secondary alcohol alkoxylate compound composition represented by the general formula (1).

These objects are accomplished by an emulsifier formed by incorporating therein a higher secondary alcohol alkoxylate compound composition represented by the general formula (1).

The objects are further accomplished by a method for the production of a higher secondary alcohol alkoxylate alkylene oxide adduct which comprises adding (poly)alkylene glycol to the double bond of a long-chain olefin thereby obtaining a higher secondary alcohol alkoxylate, and adding an alkylene oxide to the higher secondary alcohol alkoxylate thereby forming a higher secondary alcohol alkoxylate alkylene oxide adduct.

The objects are furthermore accomplished by a method for the production of an sulfuric ester composition of a higher secondary alcohol alkoxylate or a higher secondary alcohol alkoxylate alkylene oxide adduct which comprises adding (poly)alkylene glycol to the double bond of a long-chain olefin thereby obtaining a higher secondary alcohol alkoxylate, and optionally adding an alkylene oxide to the higher secondary alcohol alkoxylate thereby forming a higher secondary alcohol alkoxylate alkylene oxide adduct, sulfating the produced higher secondary alcohol alkoxylate or higher secondary alcohol alkoxylate alkylene oxide adduct, and neutralizing the resultant sulfate.

The higher secondary alcohol alkoxylate compound composition of this invention is at an advantage in having a low pour point, permitting easy handling, exhibiting a highly satisfactory permeating power, inducing perfect extinction of foam, and excelling in the deterging power and the emulsifying power. Further, the method for the production of the higher secondary alcohol alkoxylate compound according to this invention is very simple and rich in practicability and economically advantageous.

DESCRIPTION OF THE PREFERRED EMBODIMENT

Figure 1:
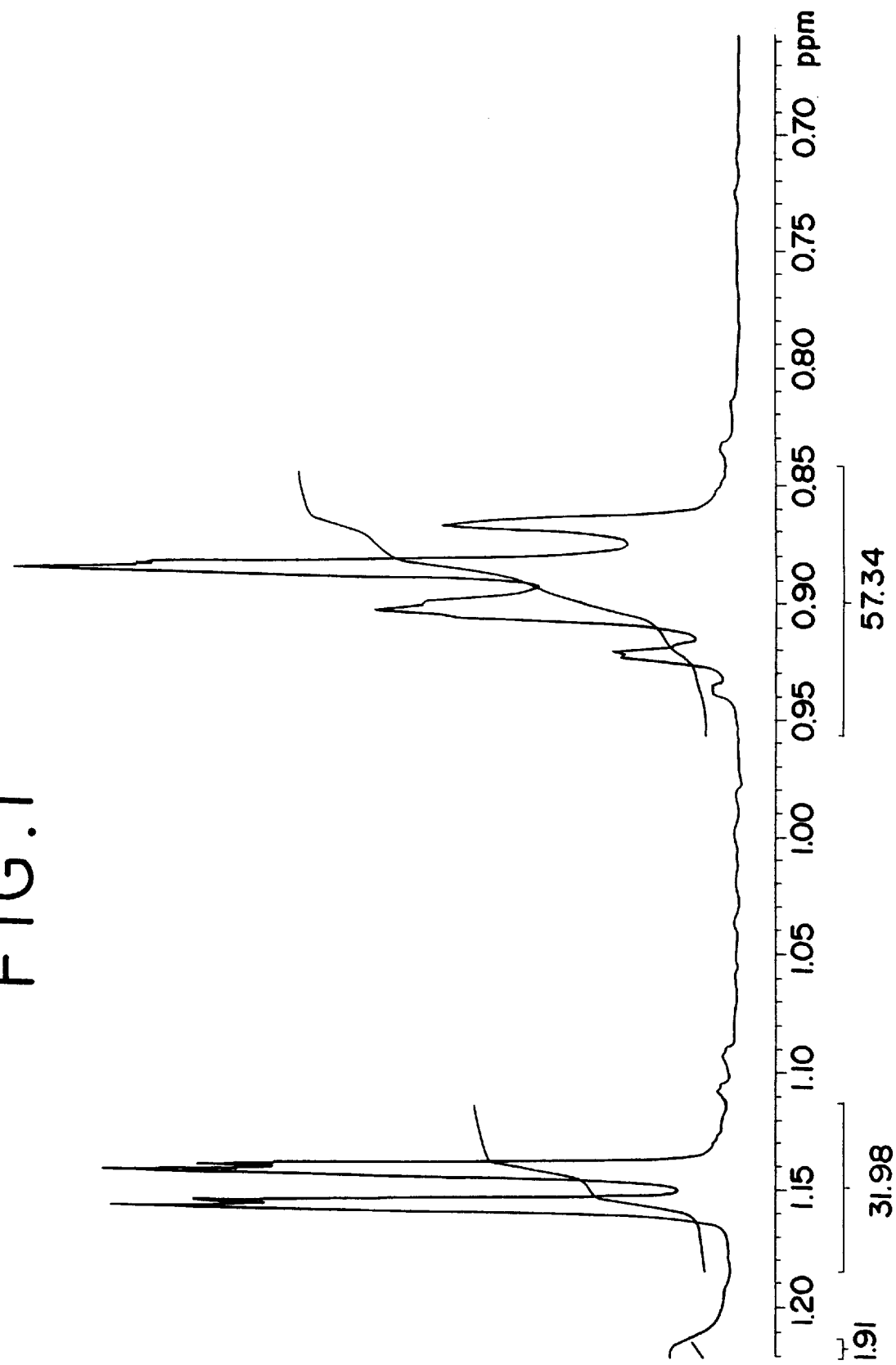
FIG. 1 represents the data of $^1$H-NMR analysis used for the calculation of the positions for addition of the ethoxylate portion of the secondary dodecanol ethoxylate composition obtained in Example 1 to the alkyl chain.

The higher secondary alcohol alkoxylate compound composition according to this invention is a higher secondary alcohol alkoxylate compound composition represented by the general formula (1):

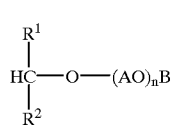

[wherein $R^1$ and $R^2$ represent an alkyl group provided that the total number of carbon atoms of $R^1$ and $R^2$ is in the range of 7 to 29 and the number of carbon atom of $R^2$ is not less than that of $R^1$ (the number of carbon atom of $R_1 \leq$ the number of carbon atom of $R_2$), A represents a lower alkylene group, n represents a numeral in the range of 1 to 50 on the average; providing that when n is not less than 2, the number of species of oxyalkylene group represented by AO maybe either one or two or more, and that when the oxyalkyl groups have two or more species, all the oxyalkylene groups are present in the average of n, and B represents a hydrogen atom or $SO_3M$ (wherein M represents an alkali metal atom, an alkaline earth metal atom, an ammonium group or a substituted ammonium group)], wherein the composition comprises 30 to 90 mol % of the higher secondary alcohol alkoxylate compound (X) having a methyl group for $R^1$ and 70 to 10 mol % of the higher secondary alcohol alkoxylate compound (Y) having an alkyl group of 2 or more carbon atoms for $R^1$.

The lower alkylene group represented by A in the general formula (1) mentioned above embraces alkylene groups of 2 to 8 carbon atoms, preferably 2 to 4 carbon atoms. As typical examples of the oxyalkylene group represented by AO, an ethoxy group, a propoxy group, a butoxy group, an isopropoxy group, a pentyloxy group, a hexyloxy group, a heptyloxy group, and an octyloxy group may be cited. Among these oxyalkylene groups cited above, an ethoxy group, a propoxy group, and a butoxy group may be preferably used. These oxyalkylene groups, as defined with respect to AO in the general formula (1) above, may comprise only one species or may otherwise comprise two or more species. The oxyalkylene groups, when comprising two or more species, may be randomly disposed or may be disposed as severally blocked. The oxyalkylene group may be constructed such that the long-chain part of an ethoxy group is formed of a propoxy group.

The alkyl groups represented by $R^1$ and $R^2$ in the general formula (1) are preferred to be straight chain alkyl groups. The total number of carbon atoms of $R^1$ and $R^2$ is in the range of 7 to 29, preferably 9 to 19, and at the same time, the number of carbon atom of $R^2$ is not less than that of $R^1$ (the number of carbon atom of $R_1 \leq$ the number of carbon atom of $R_2$).

The symbol, n, in the general formula (1) mentioned above represents a numeral in the range of 1 to 50, preferably 1 to 20, on the average.

In the general formula (1) mentioned above, B represents a hydrogen atom or $SO_3M$. In this case, M represents an alkali metal atom, an alkaline earth metal atom, an ammonium group or a substituted ammonium group. As typical examples thereof, such alkali metal atoms as sodium, potassium and lithium, such alkaline earth metal atoms as magnesium, calcium and barium, an ammonium group, and substituted ammonium groups such as a hydroxy alkyl ammonium group and an alkyl ammonium group may be cited.

The higher secondary alcohol alkoxylate compound composition of this invention, i.e., the higher secondary alcohol alkoxylate compound composition represented by the general formula (1) mentioned above, comprises 30 to 90 mol %, preferably 40 to 80 mol %, of the higher secondary alcohol alkoxylate compound (X) having a methyl group for $R^1$ and 70 to 10 mol %, preferably 60 to 20 mol %, of the higher secondary alcohol alkoxylate compound (Y) having an alkyl group of 2 or more carbon atoms for $R^1$. In this case, if the ratio of the higher secondary alcohol alkoxylate compound (X) exceeds 90 mol %, the pour point of the obtained higher secondary alcohol alkoxylate compound composition is unduly heightened and the deterging power is degraded. On the other hand, if the ratio of the higher secondary alcohol alkoxylate compound (X) is less than 30 mol %, although the properties as the surfactant thereof is unaltered, the cost for the production is unduly high by the production method of this invention, which is disadvantageous in economical view point.

The higher secondary alcohol alkoxylate which is formed as one component of the higher secondary alcohol alkoxylate compound composition of this invention (wherein in the general formula (1), B represents a hydrogen atom) may be produced by reacting a long chain olefin of 8 to 30 carbon atoms with (poly)alkylene glycol in the presence of an acid catalyst and separating the reaction product by distillation, extraction, or some other method.

In this invention, it is essential that the long chain olefin to be used as the raw material for obtaining the higher secondary alcohol alkoxylate should be a hydrocarbon of 8 to 30 carbon atoms containing an ethylenically unsaturated bond, preferably a noncyclic hydrocarbon of 10 to 20 carbon atoms containing an ethylenically unsaturated bond. As typical examples of the long chain olefin which may be used in this invention, octene, decene, dodecene, tetradecene, hexadecene, octadecene, eicocene, dococene, tetracocene, hexacocene, octacocene, and triaconcene, for example, 1-decene, 2-decene, 1-dodecene, 2-dodecene, 3-dodecene, 4-dodecene, 5-dodecene, 1-tetradecene, 2-tetradecene, and 1-hexadecene maybe cited. Among these long chain olefins, decene, dodecene, tetradecene, hexadecene, octadecene, and eicocene may be preferably used. These long chain olefins may be used either singly or in the form of a mixture of two or more members.

Further, the long chain olefin may be used without any restriction, and be either such a long chain olefin as those having an unsaturated bond at an a position, such a long chain olefin as those having an unsaturated bond at an inner position, or a mixture of a long chain olefin having an unsaturated bond at an α position with a long chain olefin having an unsaturated bond at an inner position. Needless to say, two or more long chain olefins having unsaturated bonds at different positions maybe used in combination.

As typical examples of the (poly)alkylene glycol which may be used as the raw material for obtaining the higher secondary alcohol alkoxylate, monoethylene glycol, diethylene glycol, triethylene glycol, polyethylene glycol, monopropylene glycol, dipropylene glycol, tripropylene glycol, polypropylene glycol, 1,3-propane diol, 1,2-butane diol, 2,3-butane diol, 1,4-butane diol, 1,6-hexane diol, paraxylene glycol, and 1,4-cyclohexane methane diol may be cited. These (poly)alkylene glycols may be used either singly or in the form of a mixture of two or more members.

Although the molar ratio of the (poly)alkylene glycol to the long chain olefin is not particularly limited, it is preferably in the range of 0.05 to 20, more preferably in the range of 0.1 to 10. If the molar ratio is less than 0.05, the yield of the higher secondary alcohol alkoxylate is lowered. On the other hand, if it exceeds 20, the volume of the reactor is unduly large and it is not economically advantageous. For the reaction conditions of adding the (poly)alkylene glycol to the unsaturated bond of the long chain olefin, the reaction temperature is generally in the range of 50° to 250° C., preferably 100° to 200° C., and the reaction pressure may be either reduced pressure, normal pressure, or applied pressure, but desirably falls within the range of normal pressure to 20 kg/cm². If the temperature is less than 50° C., the reaction velocity is unduly low. On the other hand, if it exceeds 250° C., such disadvantages as that the polymerization of the long chain olefin, the degradation or condensation polymerization of the (poly)alkylene glycol be occurred and consequently the selectivity is lowered.

As typical examples of the acid catalyst to be used for the reaction of the long chain olefin with the (poly)alkylene glycol, strongly acidic ion-exchange resins, crystalline aluminosilicate such as BEA type zeolite, and dodecyl benzene sulfonic acid may be cited. Among these acid catalysts, crystalline aluminosilicate, particularly BEA type zeolite, proves to be advantageous in terms of reactivity.

The amount of the acid catalyst be used is in the range of 1 to 50% by weight, preferably 2 to 30% by weight, based on the amount of the long chain olefin. If the amount of the catalyst mentioned above is less than 1% by weight, the catalyst will produce no satisfactory catalytic activity and will not be capable of promoting the addition reaction. Conversely, if it exceeds 50% by weight, the excess will bring about no proportionate addition to the effect and will not do any good economically.

The higher secondary alcohol alkoxylate can be used in its unmodified form as the raw material for the sulfuric ester of the higher secondary alcohol alkoxylate, while it can be converted into the higher secondary alcohol alkoxylate alkylene oxide adduct according to this invention by reacting with an alkylene oxide such as, for example, ethylene oxide, propylene oxide, butylene oxide, and styrene oxide in the presence of an alkali catalyst. This higher secondary alcohol alkoxylate alkylene oxide adduct can be used in its unmodified form as the raw material for the sulfuric ester of the higher secondary alcohol alkoxylate alkylene oxide adduct according to this invention.

The addition mole number of the alkylene oxide added to the higher secondary alcohol alkoxylate, although is not particularly limited, is in the range of 1 to 30, preferably 4 to 20. As respects the conditions for the addition of this alkylene oxide, the reaction temperature is generally in the range of 50° to 250° C., preferably 100° to 200° C. and the reaction pressure may be either normal pressure or an increased pressure, preferably in the range of normal pressure to 20 kg/cm$^2$. If the reaction temperature is lower than 50° C., the reaction velocity will be unduly low. Conversely, if it exceeds 250° C., the disadvantage of the increase of the amount of the product generated by decomposition and secondary reaction will ensue.

As typical examples of the alkali catalyst mentioned above, hydroxides of alkali metals or alkaline earth metals including sodium hydroxide, potassium hydroxide, lithium hydroxide, magnesium hydroxide, calcium hydroxide, and barium hydroxide may be cited. Among these alkali catalysts, sodium hydroxide and potassium hydroxide prove to be particularly advantageous in view of ease of procurement and reactivity. These alkali catalysts may be added in the form of powder, granules or an aqueous solution, or may be dehydrated. The amount of such an alkali catalyst to be used is in the range of 0.01 to 2.0% by weight, preferably 0.02 to 0.5% by weight, based on the amount of the alkoxylate as the raw material.

The sulfuric ester composition of the higher secondary alcohol alkoxylate or the higher secondary alcohol alkoxylate alkylene oxide adduct of this invention can be obtained either by sulfating the above higher secondary alcohol alkoxylate or the alkylene oxide adduct thereof and neutralizing the reaction mixture with a basic substance, or by sulfating the above higher secondary alcohol alkoxylate or the alkylene oxide adduct thereof in the presence of a solvent, neutralizing the reaction mixture with a basic substance, removing the solvent therefrom. In this sulfation process, chlorosulfonic acid or sulfuric anhydride may be used.

When the chlorosulfonic acid is used, the sulfation may be carried out batchwise by drip-feeding chlorosulfonic acid either directly or as entrained by air or an inert gas as widely known to the higher secondary alcohol alkoxylate or the alkylene oxide adduct thereof, or by mixing them by the method disclosed in JP-B-01-36,823, namely by the use of a sulfating device provided with an external circulator incorporating a line mixer therein. The duration for drip-feeding chlorosulfonic acid is in the range of one to two hours and the reaction temperature is in the range of −20° to 30° C., preferably 0° to 20° C.

When the sulfuric anhydride is used, the sulfation may be carried out continuously by the method disclosed in JP-B-51-17,538, i.e. by causing the higher secondary alcohol alkoxylate or the alkylene oxide adduct thereof to flow down in the form of a thin film and meanwhile allowing sulfuric anhydride gas diluted with an inert gas to flow parallelly to the thin film and come into gas-liquid contact therewith by means of a parallel flow thin film reacting device. The flow rate of the inert gas is in the range of 20 to 70 m per second, the sulfuric anhydride concentration in the gas is in the range of 1 to 10% by volume, and the molar ratio of the sulfuric anhydride to the higher secondary alcohol alkoxylate is preferred to be in the range of 0.95 to 1.2. The reaction temperature is in the range of −20° to 60° C., preferably 0° to 30° C.

The sulfuric ester composition of the higher secondary alcohol alkoxylate or the alkylene oxide adduct thereof according to this invention can be manufactured with higher quality in a higher yield by using a solvent during the sulfation process. As typical examples of the solvent to be used herein, chlorine type solvents such as chloroform, carbon tetrachloride, ethylene chloride, 1,1,1-trichloroethane, and 1,1,1,2-tetrachloroethane; hydrocarbon type solvents such as n-pentane, n-hexane, n-heptane, and cyclohexane; and ether type solvents such as diethyl ether and isopropyl ether may be cited. The solvent concentration is preferred to be in the range of 10 to 90% by weight, based on the amount of the reaction solution. If the solvent concentration is less than 10% by weight, the effect by the use of the solvent cannot be attained. If it exceeds 90% by weight, the disadvantage of impairing the reaction efficiency and lowering the yield will ensue.

The basic substance which is suitable for the neutralization step includes alkali metal hydroxides, preferably sodium hydroxide, potassium hydroxide, and lithium hydroxide, oxides and hydroxides of alkaline earth metals, preferably magnesium oxide, magnesium hydroxide, calcium oxide, and calcium hydroxide, and ammonia and alkanol amines, preferably mono-, di-, and tri-ethanolamines and primary, secondary, and tertiary alkyl amines containing 1 to 4 carbon atoms per alkyl group, for example.

As respects applications, the higher secondary alcohol alkoxylate compound composition represented by the general formula (1) of this invention can be used as nonionic surfactants and as raw materials for the production of anionic surfactants and cationic surfactants as well. Since it shows a low pour point, permits easy handling, exhibits highly satisfactory permeating power, induces perfect extinction of foam, and excels in deterging power and emulsifying power, it can be preferably used as a detergent and an emulsifier.

According to another aspect of the present invention, therefore, a detergent which comprises the higher secondary alcohol alkoxylate compound composition mentioned above is provided. The detergent contemplated by this invention may use the higher secondary alcohol alkoxylate compound composition mentioned above either alone or in combination with any of the heretofore known detergent grade surfactants. As typical examples of the surfactants, anionic surfactants such as of alkyl benzene sulfonates, alkyl sulfuric esters, α-olefin sulfonates, alkyl sulfonates, aliphatic amide sulfonates, dialkyl sulfosuccinates, and alkyl ether sulfuric esters; cationic surfactants such as of alkyl amine salts and quaternary ammonium salts; and amphoteric surfactants such as of alkyl betaines may be cited.

The higher secondary alcohol alkoxylate or the alkylene oxide adduct thereof which has a hydrogen atom for B in the general formula (1) may additionally incorporate therein any of the conventional nonionic surfactants such as, for example, a higher primary alcohol ethoxylate in an amount such that the quality inherent in the detergent of this invention is not impaired.

The sulfate of the higher secondary alcohol alkoxylate or the alkylene oxide adduct thereof which has SO$_3$M for B in the general formula (1) may additionally incorporate therein any of the conventional anionic surfactants such as, for example, an alkyl aryl sulfonate, a higher primary alcohol sulfuric ester, or a higher primary alkyl ether sulfuric ester in an amount such that the quality inherent in the detergent of this invention is not impaired.

Further, the detergent of this invention may further incorporate therein various additives which are generally used in standard detergents. As typical examples of the additives, alkali agents, builders, perfumes, fluorescent whitening agents, coloring agents, foaming agents, foam stabilizers, lustering agents, fungicides, bleaching agents, enzymes, antiseptics, dyes, and solvents may be cited.

The detergent of this invention can be effectively used as detergents for clothes, textile products, tableware, containers, sundry utensils, foodstuffs, products for building maintenance, dwellings, furniture, automobiles, aircraft, and metal products, and as shampoos and body shampoos.

According to the further aspect of this invention, an emulsifier which comprises the higher secondary alcohol alkoxylate compound composition mentioned above is provided. The emulsifier contemplated by this invention may use the higher secondary alcohol alkoxylate compound composition mentioned above either alone or in combination with any of the heretofore known emulsifiers. As typical examples of the emulsifier, anionic surfactants, cationic surfactants, nonionic surfactants, and amphoteric surfactants may be cited.

The oily substance to be used in the emulsifier of this invention is not particularly defined but may embrace mineral oils, animal and plant oils, and synthetic oils. These oily substances may be used either singly or in the form of a mixture of two or more members. As typical examples of the mineral oil, spindle oil, machine oil, and liquid paraffin may be cited. As typical examples of the animal and plant oils, beef tallow, lard, fish oil, whale oil, rapeseed oil, sesame oil, coconut oil, soybean oil, palm oil, tsubaki oil, and castor oil may be cited.

The emulsifier of this invention can be used in agricultural pesticides, metal working oils, and coating materials and as an emulsifier for emulsion polymerization.

Now, this invention will be described more specifically below with reference to working examples. It should be noted, however, this invention is not limited to these working examples. In the following working examples, compositions having 1 for n in the general formula (1) will be referred to as "higher secondary alcohol alkoxylates" and compositions having not less than 2 for n to as "higher secondary alcohol alkoxylate alkylene oxide adducts".

Method for Synthesis

EXAMPLE 1

Secondary Dodecanol Ethoxylate Composition

A reaction vessel of glass, 3000 ml in inner volume, provided with stirring vanes and a reflux condenser was charged with 810 g (4.82 mols) of a dodecene-isomer mixture (composed of 25 mol % of 1-dodecene and 75 mol % of inner dodecene) obtained by causing 1-dodecene to react in the liquid phase with 5% by weight of a BEA type zeolite (produced by PQ Corp. and marketed under trademark designation of "VALFOR CP 811 BL-25") at 150° C. for 10 hours, 900 g (14.52 mols) of monoethylene glycol, and 100 g of the BEA type zeolite (produced by PQ Corp. and marketed under trademark designation of "VALFOR CP 811 BL-25"). The vapor-phase part of the reaction vessel was displaced with nitrogen and then retained in the atmosphere of nitrogen at normal pressure. The reaction mixture was heated to and kept at 150° C. for three hours and meanwhile kept stirred at 600 rpm to induce reaction. The reaction solution was cooled to room temperature. The dodecene phase in the upper layer was separated and distilled to expel the unaltered dodecene. The residue of the distillation was treated under a reduced pressure of 2 mmHg in a boiling point range of 129° to 131° C., to obtain 155 g of a secondary dodecanol ethoxylate composition.

The positions for addition of the ethoxylate portion of the resultant secondary dodecanol ethoxylate composition to the alkyl chain was determined based on the proton ratio of the alkyl terminal methyl group by the $^1$H-NMR analysis (FIG. 1). Consequently, the ratio of the secondary alcohol ethoxylate composition [ethoxylate having a methyl group for $R^1$ in the general formula (1)] having the second position ethoxylated (which corresponds to the higher secondary alcohol alkoxylate compound (X) in claim 1; and it is similarly applied hereinunder) was found to be 71 mol %. When this secondary alcohol ethoxylate composition was tested for the pour point in accordance with the method specified in JIS (Japanese Industrial Standard) K-2269, it was found to be not higher than −20° C.

Method for the Calculation of the Position of Ethoxide or Sulfuric Ester

Integral value of doublet near 1.15 ppm (protons of the methyl group of $R^1$ representing a methyl group): a Integral value of triplet near 0.9 ppm (protons of the terminal methyl group of $R^1$ representing an alkyl group of not less than 2 carbon atoms and all the terminal methyl groups of $R^2$): b Ratio of higher secondary alcohol alkoxylate compound (X): c $$c=2a/(a+b)$$

Method for NMR Analysis

Apparatus: Varian UNITY Plus 400 (400 MHz)
Solvent: $CDCl_3$+0.03% TMS:Sample=99:1
Number of rounds of integration: 16
The conditions displayed after $^1$H-NMR analysis were as follows:
Frequency: 399.958 MHz
Spectral width: 7998.4 Hz
Acquisition time: 4.001 sec
Relaxation delay: 3.000 sec
Pulse width: 10.0 usec
Ambient temperature
Number of repetitions: 16
Double precision acquisition
Data Processing
FT size: 65536
Total acquisition time: 1 minute

EXAMPLE 2

Secondary Dodecanol Ethoxylate Ethylene Oxide Adduct Composition

An autoclave of stainless steel was charged with 155 g (0.67 mol) of the secondary dodecanol ethoxylate obtained in Example 1 and 0.2 g of sodium hydroxide as a catalyst. The gaseous phase part of the autoclave was displaced with nitrogen and then adjusted to an inner pressure of 1.0 kg/cm$^2$ G with nitrogen. Then, the autoclave was heated to 150° C.

and 217 g (4.93 mols) of ethylene oxide was introduced into the autoclave over a period of three hours. After this introduction, the autoclave was kept at 150° C. for one hour and then cooled to room temperature and relieved of the inner pressure. Consequently, a secondary dodecanol ethoxylate ethylene oxide adduct composition having an average of 8.4 for n in the general formula (1) was obtained.

Figure 2:
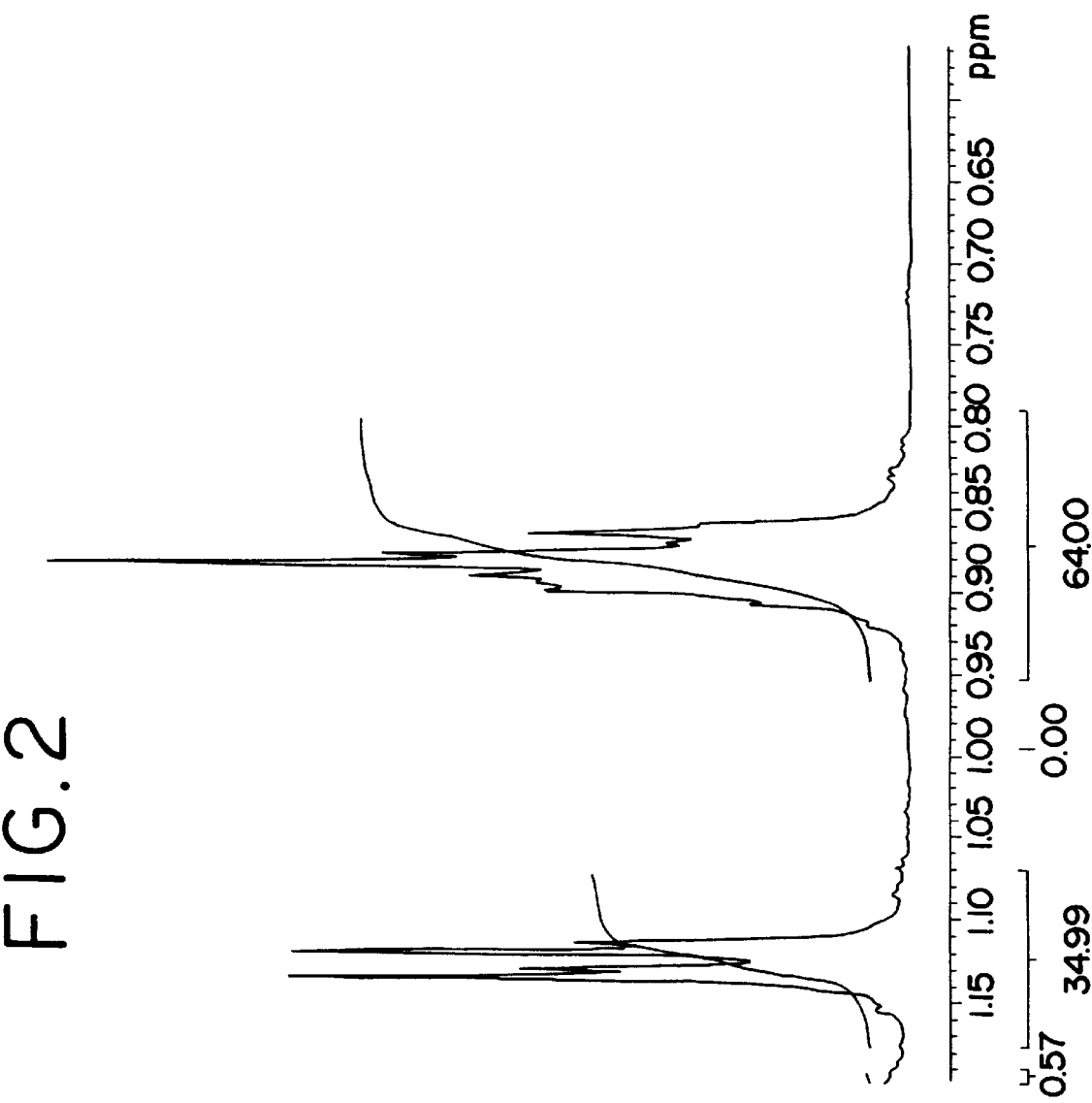
FIG. 2 represents the data of $^1$H-NMR analysis used for the calculation of the positions for addition of the ethoxylate portion of the secondary dodecanol ethoxylate ethylene oxide adduct composition obtained in Example 2 to the alkyl chain.

The positions for addition of the ethoxylate portion of the resultant secondary dodecanol ethoxylate ethylene oxide adduct composition to the alkyl chain was determined based on the proton ratio of the alkyl terminal methyl group by the $^1$H-NMR analysis (FIG. 2). Consequently, the ratio of the secondary alcohol ethoxylate ethylene oxide adduct having the second position ethoxylated was found to be 72 mol %. The method for the calculation of the position of ethoxylation and the method for the NMR analysis were the same as those of Example 1.

EXAMPLE 3

Secondary Tetradecanol Ethoxylate Composition

A reaction vessel of glass, 3000 ml in inner volume, provided with stirring vanes and a reflux condenser was charged with 810 g (4.13 mols) of a tetradecene-isomer mixture (composed of 20 mol % of 1-tetradecene and 80 mol % of inner tetradecene) obtained by causing 1-tetradecene to react in the liquid phase with 5% by weight of a BEA type zeolite (produced by PQ Corp. and marketed under trademark designation of "VALFOR CP 811 BL-25") at 150° C. for 13 hours, 900 g (14.52 mols) of monoethylene glycol, and 100 g of the BEA type zeolite (produced by PQ Corp. and marketed under trademark designation of "VALFOR CP 811 BL-25"). The vapor-phase part of the reaction vessel was displaced with nitrogen and then retained in the atmosphere of nitrogen at normal pressure. The reaction mixture was heated to and kept at 150° C. for three hours and meanwhile kept stirred at 600 rpm to induce reaction. The reaction solution was cooled to room temperature. The tetradecene phase in the upper layer was separated and distilled.

The residue of the distillation was treated under a reduced pressure of 5 mmHg in a boiling point range of 170° to 174° C. to obtain 102 g of a secondary tetradecanol ethoxylate composition.

Figure 3:
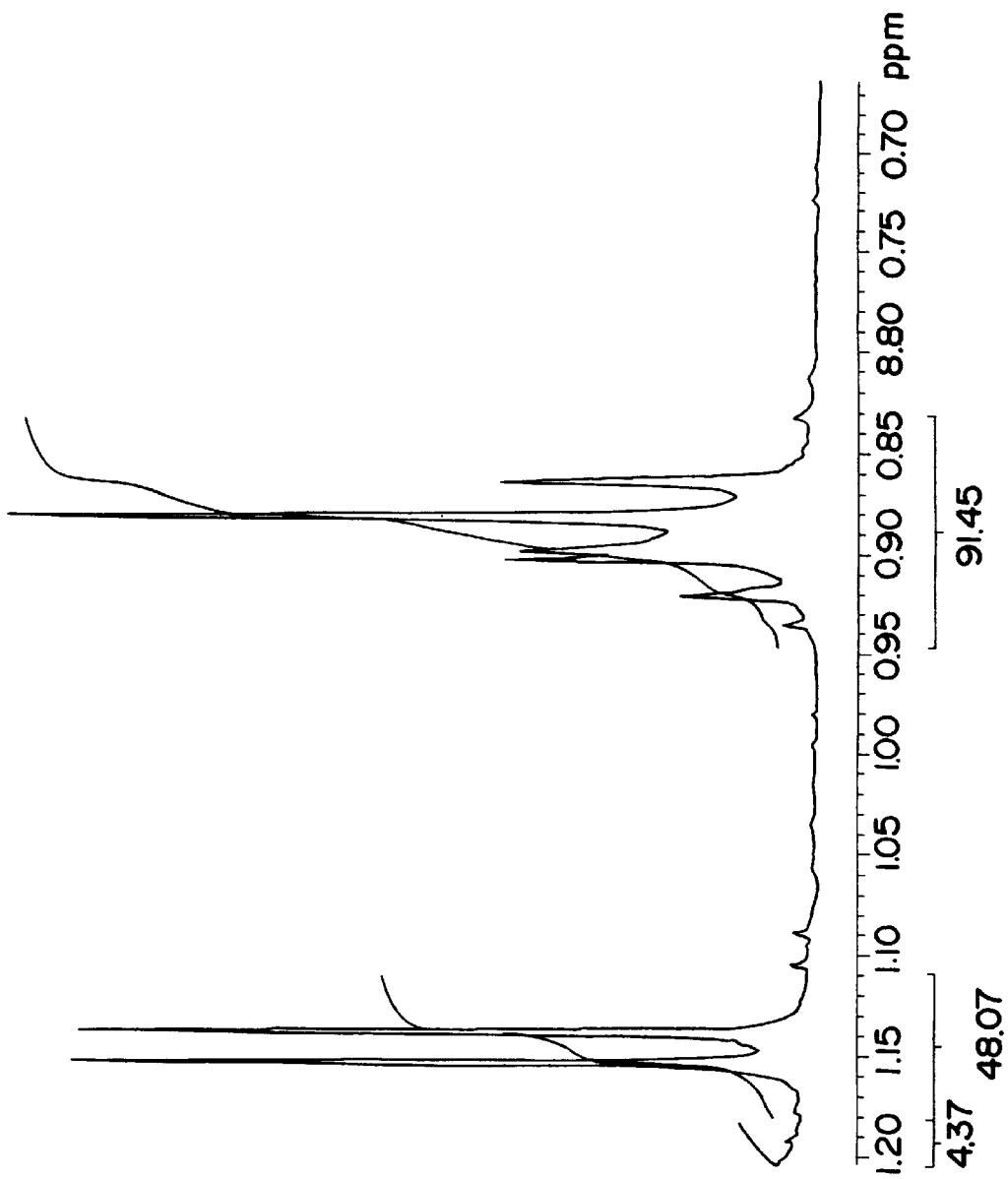
FIG. 3 represents the data of $^1$H-NMR analysis used for the calculation of the positions for addition of the ethoxylate portion of the secondary tetradecanol ethoxylate composition obtained in Example 3 to the alkyl chain.

The positions for addition of the ethoxylate portion of the resultant secondary tetradecanol ethoxylate composition to the alkyl chain was determined based on the proton ratio of the alkyl terminal methyl group by the $^1$H-NMR analysis (FIG. 3). Consequently, the ratio of the secondary alcohol ethoxylate having the second position ethoxylated was found to be 69 mol %. The method for the calculation of the position of ethoxylation and the method for the NMR analysis were the same as those of Example 1. When the secondary alcohol ethoxylate composition was tested for the pour point in accordance with the method specified in JIS K-2269, it was found to be −10° C.

EXAMPLE 4

Secondary Tetradecanol Ethoxylate Ethylene Oxide Adduct Composition

An autoclave of stainless steel was charged with 102 g (0.40 mol) of the secondary tetradecanol ethoxylate composition obtained in Example 3 and 0.2 g of sodium hydroxide as a catalyst. The gaseous phase part of the autoclave was displaced with nitrogen and then adjusted to an inner pressure of 1.0 kg/cm$^2$ G with nitrogen. Then, the autoclave was heated to 150° C. and 150 g (3.42 mols) of ethylene oxide was introduced into the autoclave over a period of three hours. After this introduction, the autoclave was kept at 150° C. for one hour and then cooled to room temperature and relieved of the inner pressure. Consequently, a secondary tetradecanol ethoxylate ethylene oxide adduct composition having an average of 9.6 for n in the general formula (1) was obtained.

Figure 4:
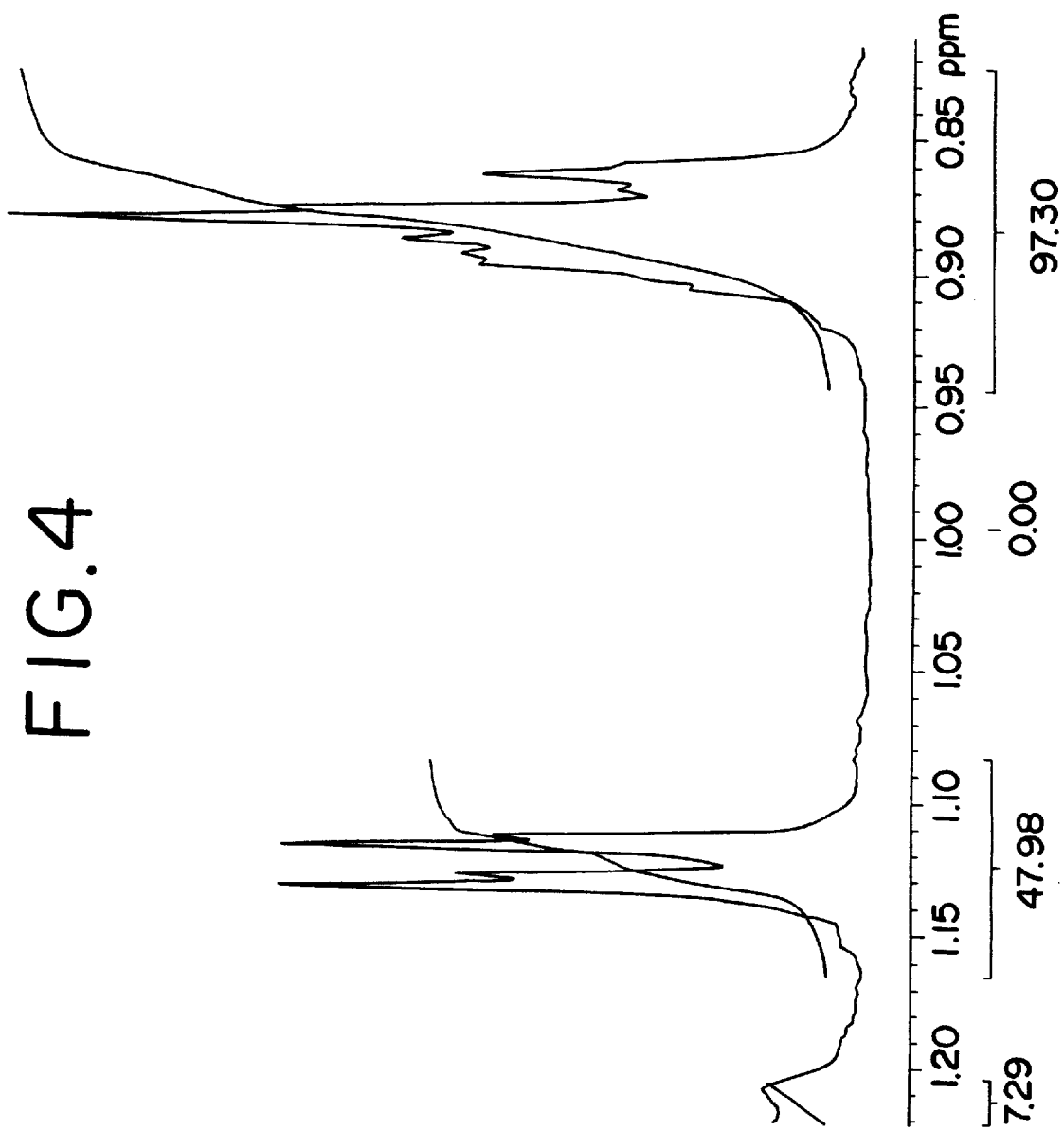
FIG. 4 represents the data of $^1$H-NMR analysis used for the calculation of the positions for addition of the ethoxylate portion of the secondary tetradecanol ethoxylate ethylene oxide adduct composition obtained in Example 4 to the alkyl chain.

The positions for addition of the ethoxylate portion of the resultant secondary tetradecanol ethoxylate ethylene oxide adduct composition to the alkyl chain was determined based on the proton ratio of the alkyl terminal methyl group by the $^1$H-NMR analysis (FIG. 4). Consequently, the ratio of the secondary alcohol ethoxylate ethylene oxide adduct composition having the second position ethoxylated was found to be 66 mol %. The method for the calculation of the position of ethoxylation and the method for the NMR analysis were the same as those of Example 1.

CONTROL 1

Primary Dodecanol Ethoxylate Ethylene Oxide Adduct

An autoclave of stainless steel was charged with 320 g (1.7 mols) of n-dodecanol and 0.2 g of sodium hydroxide as a catalyst. The gaseous phase part of the autoclave was displaced with nitrogen and then adjusted to an inner pressure of 1.0 kg/cm$^2$ G with nitrogen. Then, the autoclave was heated to 150° C. and 680 g (15.5 mols) of ethylene oxide was introduced into the autoclave over a period of three hours. After this introduction, the autoclave was kept at 150° C. for one hour and then cooled to room temperature and relieved of the inner pressure. Consequently, a primary dodecanol ethoxylate ethylene oxide adduct having an average of 9.0 for n in the general formula (1) was obtained.

CONTROL 2

Secondary Dodecanol Ethoxylate Composition

A reaction vessel of glass, 3000 ml in inner volume, provided with stirring vanes and a reflux condenser was charged with 810 g (4.82 mols) of 1-dodecene, 900 g (14.52 mols) of monoethylene glycol, and 100 g of the BEA type zeolite (produced by PQ Corp. and marketed under trademark designation of "VALFOR CP 811 BL-25"). The vapor-phase part of the reaction vessel was displaced with nitrogen and then retained in the atmosphere of nitrogen at normal pressure. The reaction mixture was heated to and kept at 150° C. for three hours and meanwhile kept stirred at 600 rpm to induce reaction. The reaction solution was cooled to room temperature. The dodecene phase in the upper layer was separated and distilled to expel the unaltered dodecene. The residue of the distillation was treated under a reduced pressure of 2 mmHg in a boiling point range of 129° to 131° C. to obtain 255 g of a secondary dodecanol ethoxylate composition.

Figure 5:
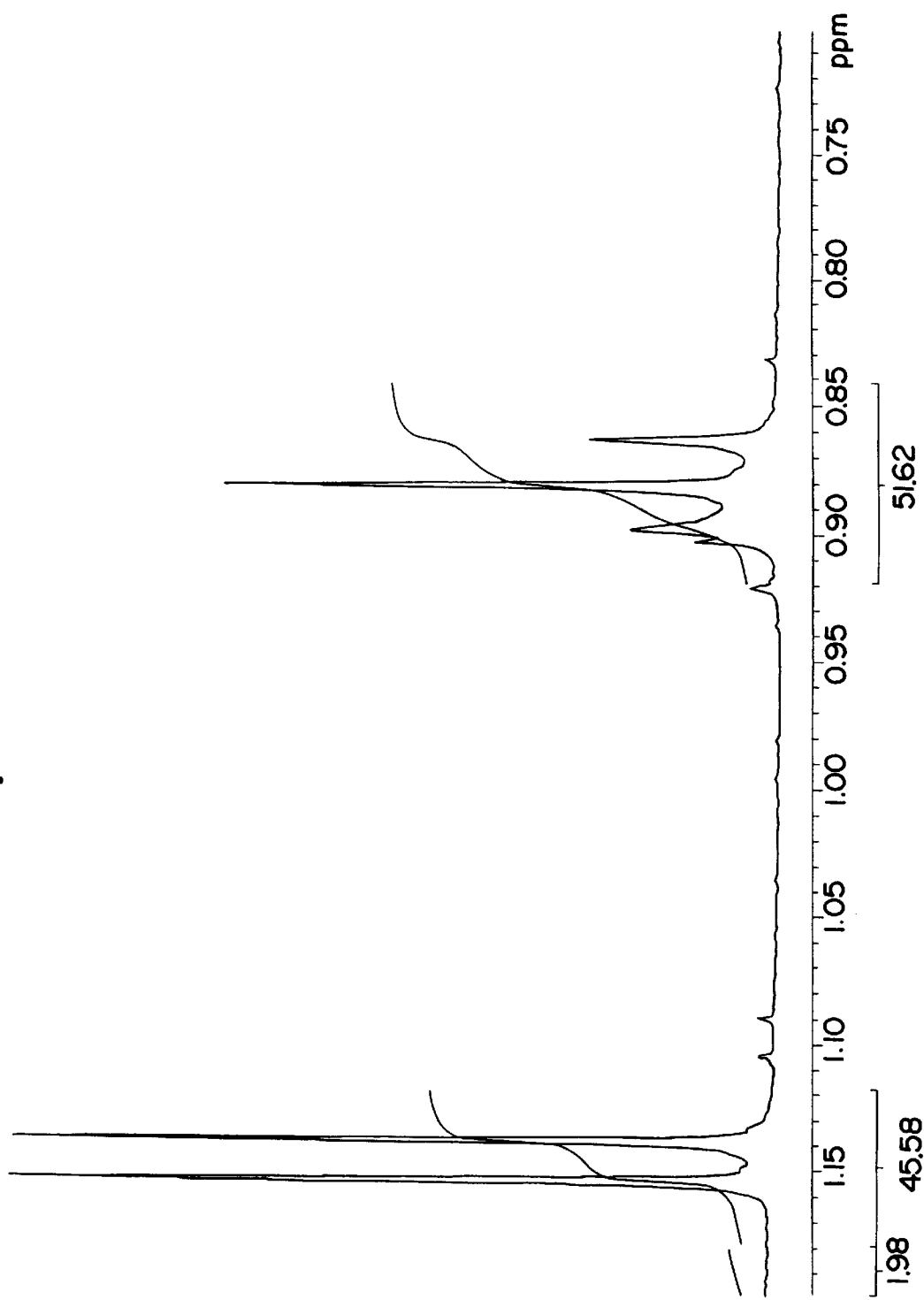
FIG. 5 represents the data of $^1$H-NMR analysis used for the calculation of the positions for addition of the ethoxylate portion of the secondary dodecanol ethoxylate composition obtained in Control 2 to the alkyl chain.

The positions for addition of the ethoxylate portion of the resultant secondary dodecanol ethoxylate composition to the alkyl chain was determined based on the proton ratio of the alkyl terminal methyl group by the $^1$H-NMR analysis (FIG. 5). Consequently, the ratio of the secondary alcohol monoethoxylate having the second position ethoxylated was found to be 94 mol %. The method for the calculation of the position of ethoxylation and the method for the NMR analysis were the same as those of Example 1.

CONTROL 3

Secondary Dodecanol Ethoxylate Ethylene Oxide Adduct

An autoclave of stainless steel was charged with 255 g (1.1 mols) of the secondary dodecanol monoethoxylate obtained in Control 2 and 0.2 g of sodium hydroxide as a catalyst. The gaseous phase part of the autoclave was displaced with nitrogen and then adjusted to an inner pressure of 1.0 kg/cm$^2$ G with nitrogen. Then, the autoclave was heated to 150° C. and 358 g (8.14 mols) of ethylene oxide was introduced into the autoclave over a period of three hours. After this introduction, the autoclave was kept at 150° C. for one hour and then cooled to room temperature and relieved of the inner pressure. Consequently, a secondary dodecanol ethoxylate ethylene oxide adduct having an average of 8.4 for n in the general formula (1) was obtained.

Figure 6:
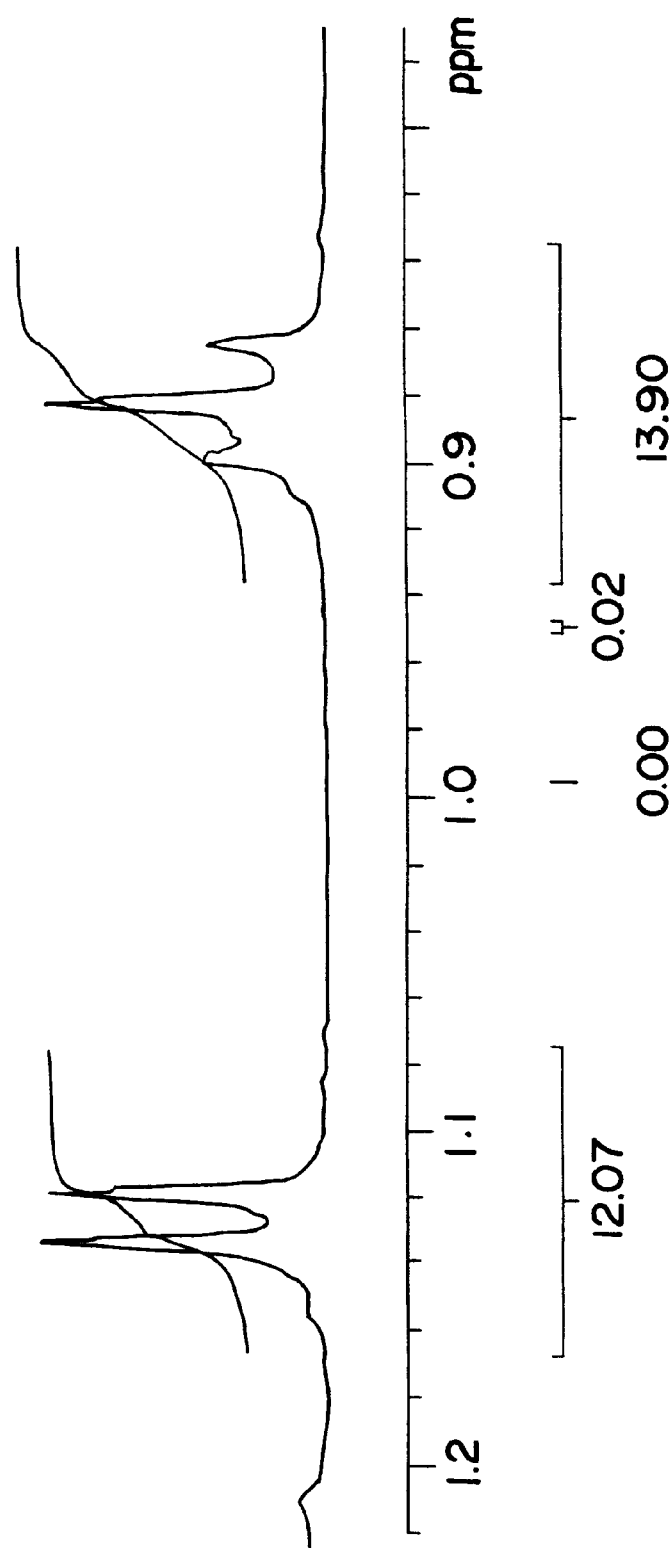
FIG. 6 represents the data of $^1$H-NMR analysis used for the calculation of the positions for addition of the ethoxylate portion of the secondary dodecanol ethoxylate ethylene oxide adduct composition obtained in Control 3 to the alkyl chain.

The positions for addition of the ethoxylate portion of the resultant secondary dodecanol ethoxylate ethylene oxide adduct composition to the alkyl chain was determined based on the proton ratio of the alkyl terminal methyl group by the $^1$H-NMR analysis (FIG. 6). Consequently, the ratio of the secondary alcohol ethoxylate having the second position ethoxylated was found to be 93 mol %. The method for the calculation of the position of ethoxylation and the method for the NMR analysis were the same as those of Example 1.

EXAMPLE 5

Secondary Dodecanol Ethoxylate Sulfuric Ester Composition

By the use of a reaction tube, 5 mm in inside diameter and 100 cm in length, adapted to form a cylindrical reaction zone, the secondary dodecanol ethoxylate composition obtained in Example 1 was caused to flow via a liquid reservoir in the upper part of the reaction tube down along the inner wall of the reaction tube in the form of a thin film at a rate of 16.2 g per minute. Meanwhile, sulfuric anhydride diluted with nitrogen gas was caused to flow into the reaction tube via a nozzle disposed at the upper part of the reaction tube. The flow rate of all the nitrogen gas introduced into the reaction tube was set at 30 m per second and the concentration of the sulfuric anhydride in the total mixed gas introduced therein was set at 4% by volume. The molar ratio of the downflow of the sulfuric anhydride to the downflow of the secondary dodecanol ethoxylate was set at 1.1. The heat of reaction generated by the reaction of the ethoxylate with sulfuric anhydride was removed by the coolant flowing outside the reaction tube and kept at 15° C. The liquid effluent from the reaction tube was separated by a cyclone into nitrogen gas and the reaction product. The reaction product was immediately neutralized with an aqueous sodium hydroxide solution to obtain an aqueous solution of about 25% of sulfuric ester.

Figure 7:
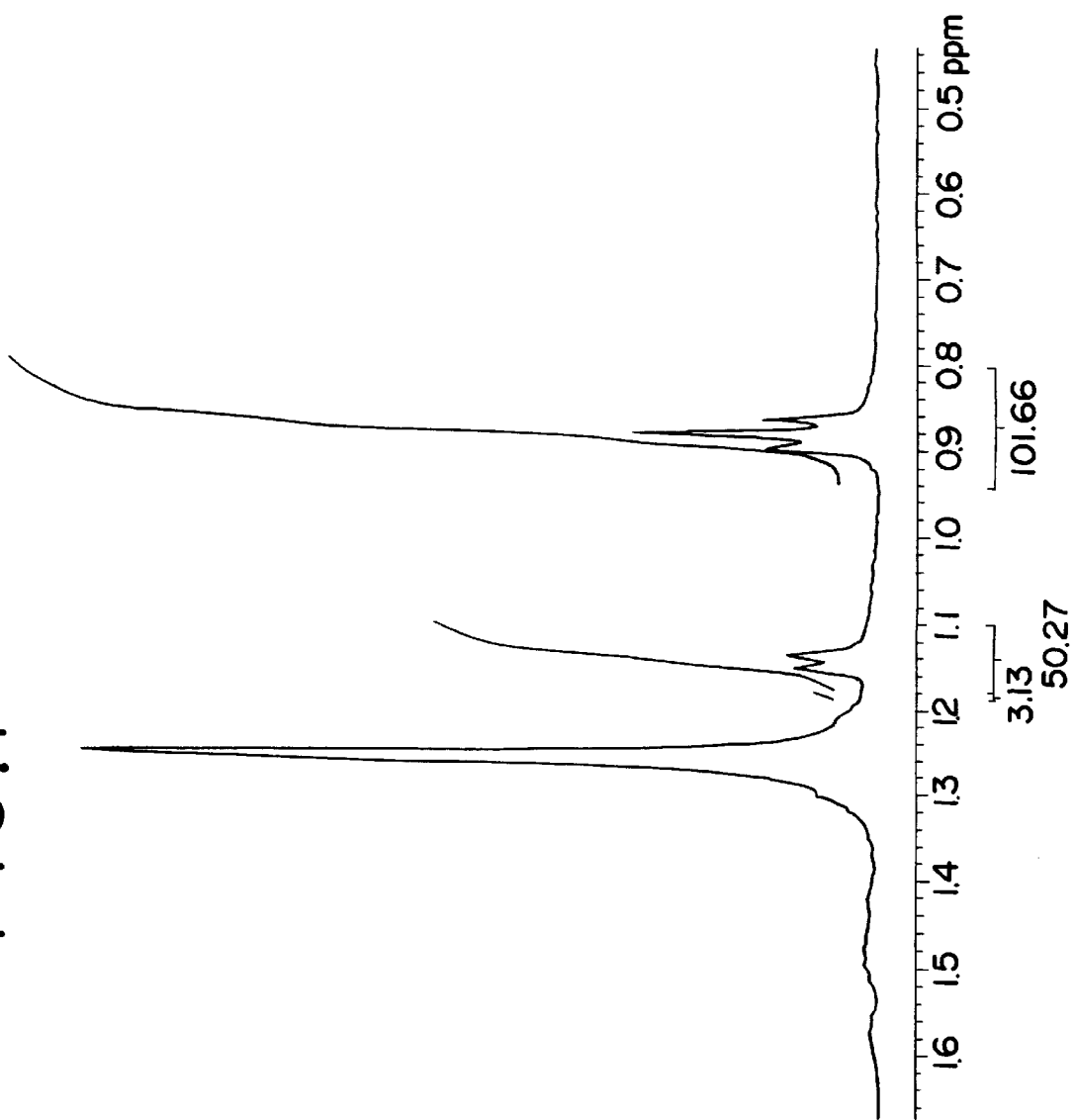
FIG. 7 represents the data of $^1$H-NMR analysis used for the calculation of the positions for addition of the sulfuric ester of the secondary dodecanol ethoxylate sulfuric ester composition obtained in Example 5 to the alkyl chain.

The positions for addition of the sulfuric ester of the resultant secondary dodecanol ethoxylate sulfuric ester composition to the alkyl chain was determined based on the proton ratio of the alkyl terminal methyl group by the $^1$H-NMR analysis (FIG. 7). Consequently, the ratio of the secondary dodecanol ethoxylate sulfuric ester having the second position sulfuric-esterified was found to be 66 mol %.

EXAMPLE 6

Secondary Dodecanol Ethoxylate Ethylene Oxide Adduct Sulfuric Ester Composition An autoclave of stainless steel was charged with 155 g (0.67 mol) of the secondary dodecanol ethoxylate composition obtained as an intermediate in Example 1 and 0.2 g of sodium hydroxide as a catalyst. The gaseous phase part of the autoclave was displaced with nitrogen and then adjusted to an inner pressure of 1.0 kg/cm$^2$ G with nitrogen. Then, the autoclave was heated to 150° C. and 62 g (1.41 mols) of ethylene oxide was introduced into the autoclave over a period of three hours. After this introduction, the autoclave was kept at 150° C. for one hour and then cooled to room temperature and relieved of the inner pressure. Consequently, a secondary dodecanol ethoxylate ethylene oxide adduct composition having an average of 3.1 mols for the oxyethylene group was obtained.

In a flask, 500 ml in inner volume, 217 g (0.67 mol) of the secondary dodecanol ethoxylate ethylene oxide adduct composition having ethylene oxide added thereto was placed and cooled to 10° C. To the cooled solution, 86.3 g (0.74 mol) of chlorosulfonic acid was drip-fed over a period of about one hour. During the drip-feeding, the liquid temperature in the flask was kept at a level in the range of 10° to 15° C. After the drip-feeding of chlorosulfonic acid, nitrogen gas was passed through the reaction solution to expel the by-produced hydrogen chloride gas. Subsequently, the reaction solution, with the temperature thereof kept at a level of not more than 20° C., was drip-fed into an aqueous sodium hydroxide solution to obtain an aqueous solution of about 25% of sulfuric ester.

Figure 8:
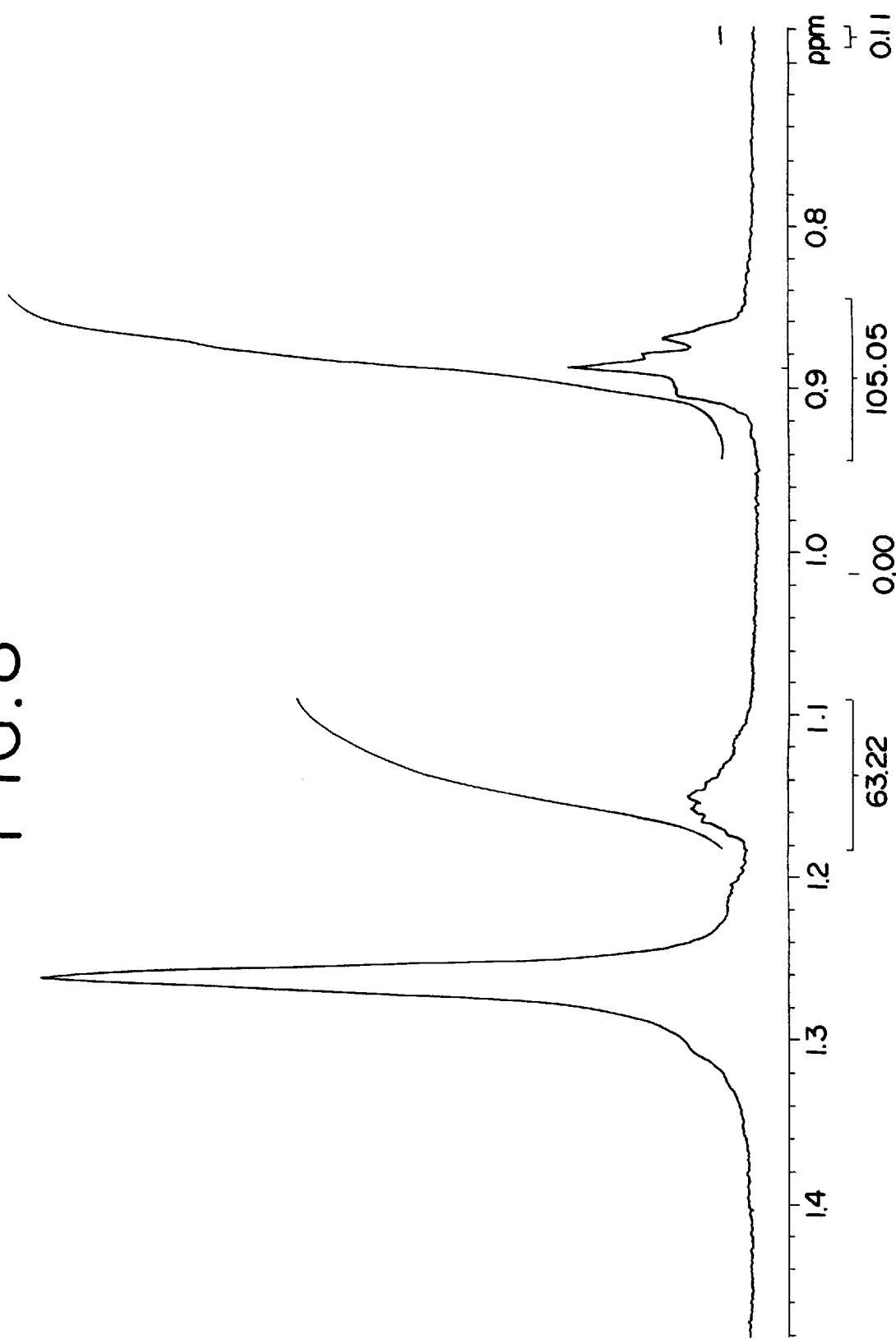
FIG. 8 represents the data of $^1$H-NMR analysis used for the calculation of the positions for addition of the sulfuric ester of the secondary dodecanol ethoxylate ethylene oxide adduct sulfuric ester composition obtained in Example 6 to the alkyl chain.

The positions for addition of the sulfuric ester of the resultant secondary dodecanol ethoxylate ethylene oxide adduct sulfuric ester composition to the alkyl chain was determined based on the proton ratio of the alkyl terminal methyl group by the $^1$H-NMR analysis (FIG. 8). Consequently, the ratio of the secondary dodecanol ethylene oxide adduct sulfuric ester having the second position sulfuric-esterified was found to be 75 mol %. The method for calculation of the position of the sulfuric ester and the method for the NMR analysis were the same as those of Example 1.

EXAMPLE 7

Secondary Hexadecanol Ethoxylate Sulfuric Ester composition

A reaction vessel of glass, 3000 ml in inner volume, provided with stirring vanes and a reflux condenser was charged with 810 g (3.62 mols) of a hexadecene-isomer mixture (composed of 20 mol % of 1-hexadecene and 80 mol % of inner hexadecene) obtained by causing 1-hexadecene to react with 5% by weight of a BEA type zeolite (produced by PQ Corp. and marketed under trademark designation of "VALFOR CP 811 BL-25") at 150° C. for 13 hours, 900 g (14.52 mols) of monoethylene glycol, and 100 g of the BEA type zeolite (produced by PQ Corp. and marketed under trademark designation of "VALFOR CP 811 BL-25"). The vapor-phase part of the reaction vessel was displaced with nitrogen and then retained in the atmosphere of nitrogen at normal pressure. The reaction mixture was heated to and kept at 150° C. for three hours and meanwhile kept stirred at 600 rpm to induce reaction. The reaction solution was cooled to room temperature. The hexadecene phase in the upper layer was separated and distilled to expel the unaltered hexadecene. The residue of the distillation was treated under a reduced pressure of 2 mg in a boiling point range of 160° to 165° C. to obtain 95 g of a secondary hexadodecanol ethoxylate composition.

In a flask, 1 liter in inner volume, 80 g (0.28 mol) of the secondary hexadecanol ethoxylate composition and 400 g of ethylene chloride as a solvent were placed and cooled to 10° C. Into the cooled solution, 36 g (0.31 mol) of chlorosulfonic acid was drip-fed over a period of about one hour. During this drip-feeding, the liquid temperature was kept at a level in the range of 10° to 15° C. After the drip-feeding of chlorosulfonic acid, nitrogen gas was passed through the reaction solution to expel the by-produced hydrogen chloride gas. Then, the reaction solution, with the temperature kept at not more than 20° C., was drip-fed into an aqueous sodium hydroxide solution to be neutralized. The neutralized solution was deprived of ethylene chloride to obtain an aqueous solution of about 25% of sulfuric ester.

Figure 9:
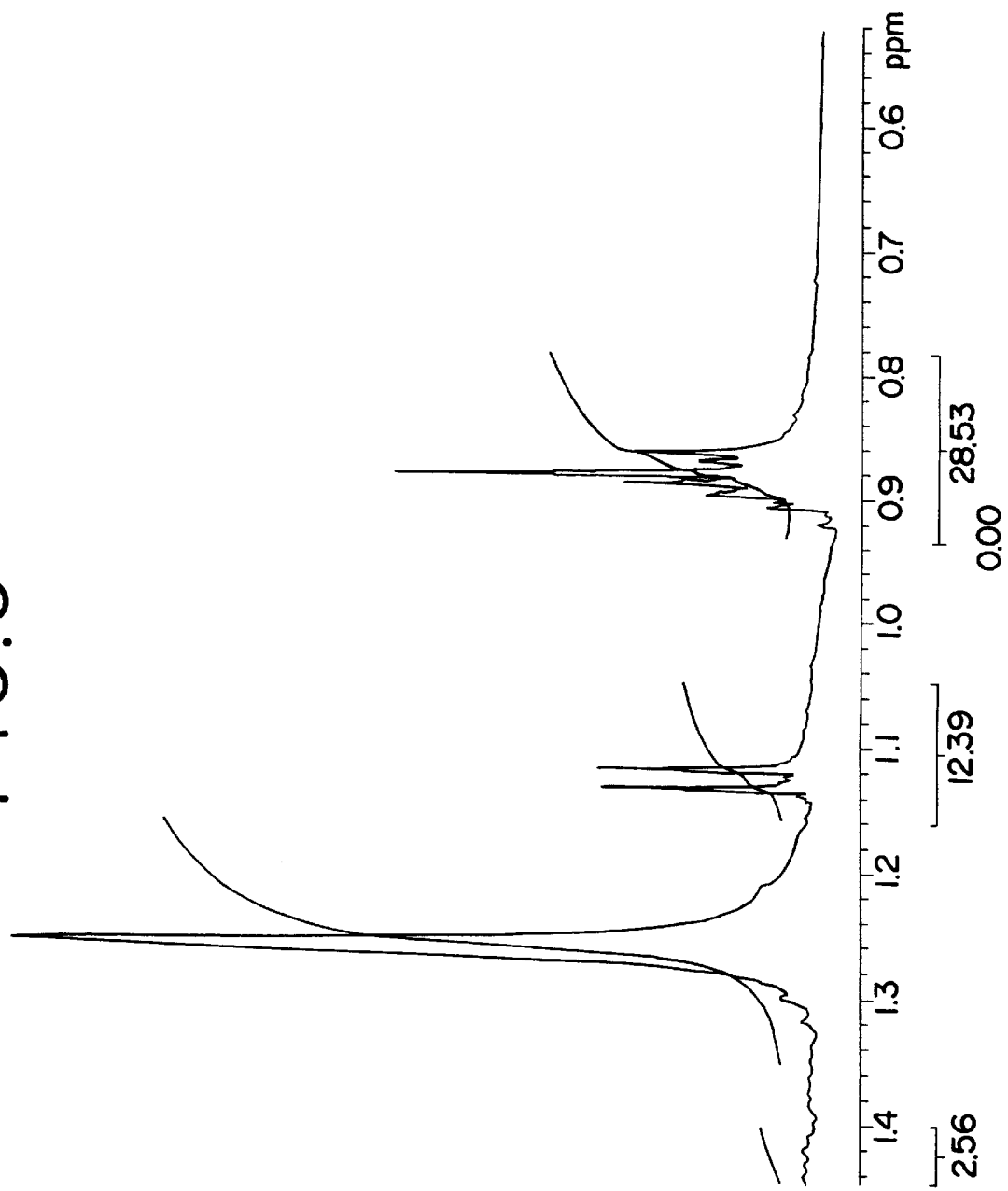
FIG. 9 represents the data of $^1$H-NMR analysis used for the calculation of the positions for addition of the sulfuric ester of the secondary hexadecanol ethoxylate sulfuric ester composition obtained in Example 7 to the alkyl chain.

The positions for addition of the sulfuric ester of the resultant secondary hexadodecanol ethoxylate sulfuric ester composition to the alkyl chain was determined based on the proton ratio of the alkyl terminal methyl group by the $^1$H-NMR analysis (FIG. 9). Consequently, the ratio of the secondary hexadecanol ethoxylate sulfuric ester having the second position sulfuric-esterified was found to be 61 mol %. The method for the calculation of the position of the sulfuric ester and the method for the NMR analysis were the same as those of Example 1.

CONTROL 4

Primary Alcohol Ethoxylate Ethylene Oxide Adduct sulfuric ester

An autoclave of stainless steel was charged with 593 g (3.08 mols) of primary alcohol (n-dodecanol/n-tetradecanol mixture) and 0.2 g of sodium hydroxide as a catalyst. The gaseous phase part of the autoclave was displaced with nitrogen and then adjusted to an inner pressure of 1.0 kg/cm$^2$ G with nitrogen. Then, the autoclave was heated to 150° C. and 407 g (9.25 mols) of ethylene oxide was introduced into the autoclave over a period of three hours. After this introduction, the autoclave was kept at 150° C. for one hour and then cooled to room temperature and relieved of the inner pressure. Consequently, a primary alcohol ethoxylate ethylene oxide adduct having an average of 3.0 mols for the ethylene oxide added was obtained.

In a flask, 500 ml in inner volume, 200 g (0.62 mol) of the primary alcohol ethoxylate ethylene oxide adduct was placed and cooled to 10° C. To the cooled solution, 79.0 g (0.68 mol) of chlorosulfonic acid was drip-fed over a period of about one hour. During the drip-feeding, the liquid temperature in the flask was kept at a level in the range of 10° to 15° C. After the drip-feeding of chlorosulfonic acid, nitrogen gas was passed through the reaction solution to expel the by-produced hydrogen chloride gas. Subsequently, the reaction solution, with the temperature thereof kept at a level below 20° C., was drip-fed into an aqueous sodium hydroxide solution to obtain an aqueous solution of about 25% of primary alcohol ethoxylate ethylene oxide adduct sulfuric ester.

CONTROL 5

Secondary Dodecanol Ethoxylate Sulfuric Ester composition

In a flask, 1 liter in inner volume, 255 g (1.11 mols) of the secondary dodecanol ethoxylate and 510 g of ethylene chloride as a solvent were placed and cooled to 10° C. Into the cooled solution, 142 g (1.22 mols) of chlorosulfonic acid was drip-fed over a period of about one hour. During this drip-feeding, the liquid temperature was kept at a level in the range of 10° to 15° C. After the drip-feeding of chlorosulfonic acid, nitrogen gas was passed through the reaction solution to expel the by-produced hydrogen chloride gas. Then, the reaction solution, with the temperature kept at not more than 20° C., was drip-fed into an aqueous sodium hydroxide solution to be neutralized to obtain an aqueous solution of about 25% of sulfuric ester.

Figure 10:
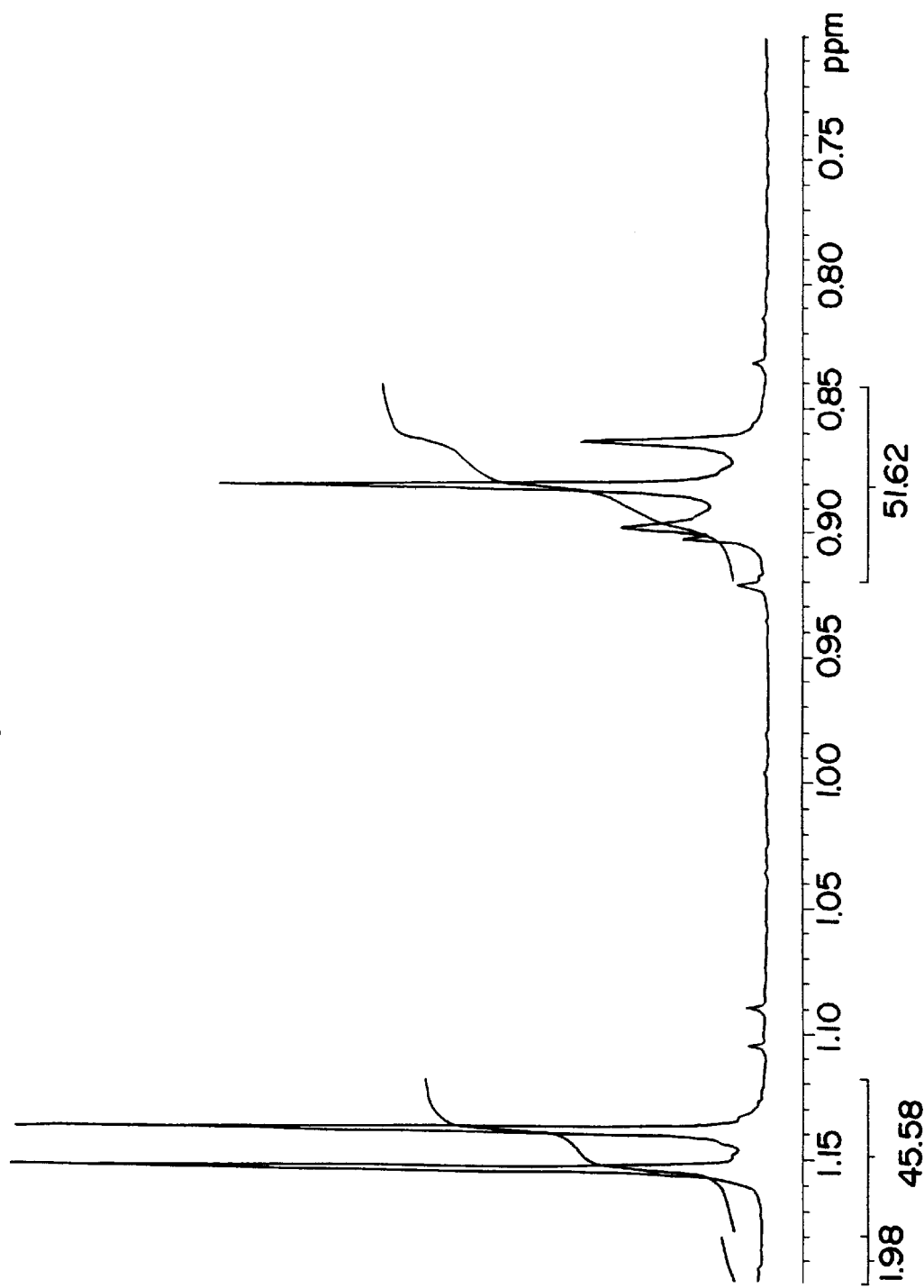
FIG. 10 represents the data of $^1$H-NMR analysis used for the calculation of the positions for addition of the sulfuric ester of the secondary dodecanol ethoxylate sulfuric ester composition obtained in Control 5 to the alkyl chain.

The positions for addition of the sulfuric ester of the resultant secondary dodecanol ethoxylate sulfuric ester composition to the alkyl chain was determined based on the proton ratio of the alkyl terminal methyl group by the $^1$H-NMR analysis (FIG. 10). Consequently, the ratio of the secondary dodecanol ethoxylate sulfuric ester composition having the second position sulfuric-esterified was found to be 94 mol %. The method for the calculation of the position of the sulfuric ester and the method for the NMR analysis were the same as those of Example 1.

EXAMPLES 8 TO 9 AND CONTROLS 6 TO 7

The substances obtained in Examples 2 and 4 and Controls 1 and 3 were tested for the following physical properties and surface properties. The results are shown in Table 1.

The physical properties and the surface properties were determined by the following methods.

(1) Pour Point

This property was determined by the method specified in JIS K-2269 (Method for testing pour point of petroleum products) with necessary modifications.

(2) Permeating Power

Wool: This property was determined at 25° C. with a sample, 90 mm×10 mm, of 20-ounce roller cloth wool piece made by Nippon Wool Textile Co., Ltd. in accordance with the method specified in JIS K-3362-1955, with necessary modifications (active agent concentration of 0.1% by weight).

Cotton: This property was determined at 25° C. in accordance with the campus disc method using cloth No. 6, with necessary modifications (active agent concentration of 0.25% by weight).

(3) Foam Behavior

This property was tested at 25° C. in accordance with the method specified in JIS K-3362 (Ross-Miles method), with necessary modifications (active agent concentration of 0.1% by weight).

TABLE 1

| Physical properties | Sample of Example 2 | Sample of Example 4 | Sample of Control 1 | Sample of Control 3 |
|---|---|---|---|---|
| Pour point (° C.) | 8 | 16 | 24 | 9 |
| Permeating power (sec) | | | | |
| Wool | 5 | 9 | 7 | 6 |
| Cotton | 9 | 15 | 14 | 10 |
| Foam behavior (cm) | | | | |
| Immed. after | 163 | 138 | 148 | 158 |
| 5 min. after | 87 | 113 | 135 | 98 |

EXAMPLES 10 TO 12 AND CONTROLS 8 TO 9

The substances obtained in Examples 5 to 7 and Controls 4 and 5 were tested for the following properties. The results are shown in Table 2.

The properties were determined by the following methods.

(1) Range of Liquid State

This magnitude was determined based on the aqueous solution viscosity tested at 25° C. by the use of a Brookfield type rotary viscometer.

(2) Surface Tension

This property was determined at 25° C. in accordance with the Wilhelmy method using a surface tension meter made by Kyowa Kagaku K.K. (active agent concentration of 0.1% by weight).

(3) Permeating Power

This property was determined with respect to cotton by following the procedure of Examples 8 and 9 (active agent concentration of 0.25% by weight).

(4) Foam Behavior

This property was determined by following the procedure of Examples 8 to 9.

TABLE 2

| | Sample of Example 5 | Sample of Example 5 | Sample of Example 7 | Sample of Control 4 | Sample of Control 5 |
|---|---|---|---|---|---|
| Range of liquid state (% by wt) | not more than 45 | — | — | not more than 30 | — |
| Surface tension (dyne/cm) | 29 | 36 | 37 | 42 | 33 |
| Permeating power (sec) of cotton | 7 | 12 | 29 | 45 | 8 |
| Foam behavior | | | | | |
| Immed. after | 198 | 183 | 185 | 192 | 187 |
| 5 min. after | 155 | 21 | 167 | 170 | 157 |

EXAMPLE 13 TO 17 AND CONTROL 10

The substances obtained in Examples 5 to 7 and Control 3 were rated for deterging power as follows. The results are shown in Table 3.

The test was performed by using a stirring type deterging power tester (Terg-O-tometer) under the following conditions while consulting the specification of JIS K-3362.

Deterging Conditions

Defiled cloth: 5 cm×5 cm

| Defiling substances (%) | |
|---|---|
| Oleic acid | 28.3 |
| Triolein | 15.6 |
| Cholesterol oleate | 12.2 |
| Liquid paraffin | 2.5 |
| Squalene | 2.5 |
| Cholesterol | 1.6 |
| Gelatin | 7.0 |
| Reddish yellow clay | 29.8 |
| Carbon black | 0.5 |

Water used: Tap water
Temperature: 25° C.
Time spent: 5 minutes for washing and 5 minutes for rinsing
Bath ratio: 3 sheets/1 pot (1 L)
Active agent concentration: 0.03%
Method for Evaluating Deterging Power Test pieces of a cloth in a freshly supplied state, an artificially defiled state, and a state cleaned with a sample detergent were tested for reflectance at three portions per test piece by the use of a reflectance meter. The deterging power (%) of the sample detergent was calculated in accordance with the following formula using the average of the numerical values of the reflectance consequently obtained.

Deterging power (%)=(Rw−Rs)/(Ro−Rs)×100 wherein Ro represents the reflectance of the freshly supplied cloth, Rs the reflectance of the artificially defiled cloth, and Rw the reflectance of the cleaned cloth.

TABLE 3

| | Sample of Example 2 | Sample of Example 4 | Sample of Example 5 | Sample of Example 6 | Sample of Example 7 | Sample of Control 3 |
|---|---|---|---|---|---|---|
| Deterging power (%) | 80 | 85 | 80 | 78 | 85 | 75 |

EXAMPLES 18 TO 20

The substances obtained in Example 2 and Examples 4 to 7 were tested for the emulsifying power as follows. The results are shown in Table 4.

The test was carried out by a procedure which comprised adding 5 ml of a synthesized sample to a mixed liquid consisting of 55 ml of water and 40 ml of oil, thoroughly mixing them, then allowing the resultant mixture to stand at rest for five minutes, and, after the standing, observing the mixture to determine the condition of separation of a water layer or an oil layer, namely the condition of emulsification. The emulsifying power of the sample was rated in terms of the condition of emulsification on the three-point scale, wherein ○: represents satisfactory condition of emulsification;
Δ: represents occurrence of slight separation; and
X: represents perfect separation of the two layers.

TABLE 4

| | Sample of Example 2 | Sample of Example 4 | Sample of Example 5 | Sample of Example 6 | Sample of Example 7 |
|---|---|---|---|---|---|
| Emulsifying power on soybean oil | ○ | ○ | ○ | ○ | ○ |
| Same on spindle oil | ○ | ○ | ○ | ○ | ○ |
| Same on ethyl acrylate | ○ | ○ | ○ | ○ | ○ |
| Same on xylene | ○ | ○ | ○ | ○ | ○ |

The entire disclosure of Japanese Patent Application Nos. 08-327365 filed on Dec. 6, 1996, 08-327366 filed on Dec. 6, 1996, 09-053212 filed on Mar. 7, 1997, and 09-053213 filed on Mar. 7, 1997 including specification, claims, drawings and summary are incorporated herein by reference in its entirety.

We claim:

1. A higher secondary alcohol alkoxylate compound composition represented by the general formula (1):

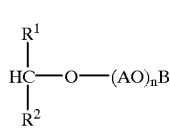

(1)

[wherein $R^1$ and $R^2$ represent an alkyl group provided that the total number of carbon atoms of $R^1$ and $R^2$ is in the range of 7 to 29 and the number of carbon atom of $R^2$ is not less than that of $R^1$ (the number of carbon atom of $R_1 \leq$ the number of carbon atom of $R_2$), A represents a lower alkylene group, n represents a numeral in the range of 1 to 50 on the average; providing that when n is not less than 2, the number of species of oxyalkylene group represented by AO may be either one or two or more, and that when the oxyalkyl groups have two or more species, all the oxyalkylene groups are present in the average of n, and B represents a hydrogen atom or $SO_3M$ (wherein M represents an alkali metal atom, an alkaline earth metal atom, an ammonium group or a substituted ammonium group)], wherein the composition comprises 30 to 90 mol % of the higher secondary alcohol alkoxylate compound (X) having a methyl group for $R^1$ and 70 to 10 mol % of the higher secondary alcohol alkoxylate compound (Y) having an alkyl group of 2 or more carbon atoms for $R^1$.

2. A composition according to claim 1, wherein in the general formula (1), said lower alkylene group represented by A is an alkylene group of 2 to 8 carbon atoms.

3. A composition according to claim 1, wherein in the general formula (1), the total number of carbon atoms of $R^1$ and $R^2$ is in the range of 9 to 19.

4. A composition according to claim 1, wherein in the general formula (1), the number of species of the oxyalkylene group represented by AO is one.

5. A composition according to claim 4, wherein said oxyalkylene group is an oxyethylene group.

6. A composition according to claim 1, wherein in the general formula (1), B represents a hydrogen atom.

7. A detergent comprising the higher secondary alcohol alkoxylate compound composition set forth in claim 1.

8. An emulsifier comprising a higher secondary alcohol alkoxylate compound composition set forth in claim 1.

9. The higher secondary alcohol alkoxylate compound composition of claim 1, wherein the composition comprises 40 to 80 mol % of the higher secondary alcohol alkoxylate compound (X) having a methyl group for $R^1$ and 60 to 20 mol % of the higher secondary alcohol alkoxylate compound (Y) having an alkyl group of 2 or more carbon atoms for $R^1$.

10. A composition according to claim 9, wherein in the general formula (1), said lower alkylene group represented by A is an alkylene group of 2 to 8 carbon atoms.

11. A composition according to claim 9, wherein in the general formula (1), the total number of carbon atoms of $R^1$ and $R^2$ is in the range of 9 to 19.

12. A composition according to claim 9, wherein in the general formula (1), the number of species of the oxyalkylene group represented by AO is one.

13. A composition according to claim 12, wherein said oxyalkylene group is an oxyethylene group.

14. A detergent comprising the higher secondary alcohol alkoxylate compound composition set forth in claim 9.

15. An emulsifier comprising a higher secondary alcohol alkoxylate compound composition set forth in claim 9.

* * * * *